US006275050B1

United States Patent
Born et al.

(10) Patent No.: US 6,275,050 B1
(45) Date of Patent: Aug. 14, 2001

(54) APPARATUS AND METHOD TO DETECT CORROSION IN METAL JUNCTIONS

(75) Inventors: Frank H. Born, Westernville, NY (US); John E. Dodge, Annandale, VA (US); William G. Duff, Fairfax Station, VA (US); Laurence J. Reynolds, Manassas, VA (US); Arlie G. Turner, Jr., Annandale, VA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/450,459

(22) Filed: Nov. 29, 1999

(51) Int. Cl.[7] .................................................. G01N 27/26
(52) U.S. Cl. ........................ 324/700; 324/623; 204/404; 205/775.5
(58) Field of Search ................... 324/700, 71.2, 324/620, 623; 204/404; 422/53; 205/775.5

(56) References Cited

U.S. PATENT DOCUMENTS

| 4,587,479 | * | 5/1986 | Rhoades et al. ................ 324/71.2 |
| 5,006,786 | * | 4/1991 | McKrube et al. ................ 324/71.2 |
| 5,180,969 | * | 1/1993 | Kwun et al. ..................... 324/71.2 |
| 5,445,719 | * | 8/1995 | Boiko ............................... 204/404 X |
| 5,647,305 | * | 7/1997 | Mulshine et al. ................ 204/404 X |

* cited by examiner

Primary Examiner—Glenn W. Brown
(74) Attorney, Agent, or Firm—Harold L. Burstyn; Joseph A. Mancini

(57) ABSTRACT

Apparatus and method to detect corrosion in metal junctions. Corroded metal junctions are usually discovered by visual inspection. The present invention detects corrosion in metal junctions when it is not visually apparent. A corroded metal junction acts as a nonlinear device. It generates harmonics and other nonlinear products (such as intermodulation) of any signals applied to the junction. The presence of relatively high level harmonics and/or intermodulation products indicates directly that corrosion has occurred. To detect corrosion in a metal junction, one couples a fundamental frequency signal ($f_0$) into the junction and tests for harmonics of that frequency, especially the third harmonic. Harmonic frequency signals that are relatively large (i.e., above the harmonics generated by the testing system) indicate the presence of corrosion. Measurements to determine if a metal junction is corroded are performed without disturbing the junction.

19 Claims, 4 Drawing Sheets

APPARATUS AND METHOD TO DETECT CORROSION IN METAL JUNCTIONS

STATEMENT OF GOVERNMENT INTEREST

The invention described herein may be manufactured and used by or for the Government for governmental purposes without the payment of any royalty thereon.

BACKGROUND OF THE INVENTION

The present invention relates to detecting corrosion in metal junctions, and, in particular, relates to detecting corrosion in metal junctions where corrosion affects current flow.

Corrosion is a significant problem for both military and commercial systems. Corrosion can cause structural failure of the corroded member. In electronic equipment, corrosion can distort or disrupt the electrical signal that propagates through a metallic connector, that is, a conductor susceptible to corrosion. Corrosion is also a significant source of Electromagnetic Interference ("EMI") that can disrupt nearby systems. Damaging levels of corrosion can be hard to detect because the corrosion may be inaccessible or imperceptible on visual inspection. The effect of corrosion on electrical transmission is generally not linear.

The failures caused by corrosion in the path of an electrical signal are often intermittent. Factors such as temperature, humidity, amount and type of use, mechanical stresses on the point of corrosion—all influence both the degree of corrosion and its effect on current flow. The rate of growth of corrosion also depends on what is corrosive in the surrounding medium. Thus, even if one knows that corrosion is present, neither the rate of growth of corrosion nor the time a system will start to fail can be predicted.

Current techniques that address corrosion fall into two categories. The first includes techniques that detect corrosion directly. The chief technique is visual inspection. X-rays can also detect the presence of foreign material, sometimes including corrosion, in metal junctions.

Visual inspection may be inadequate to identify adverse degrees of corrosion on metallic structures. The corrosion can be inaccessible, or it can be invisible to the naked eye. In electromagnetic systems even slight surface corrosion at metallic junctions can impede current flow. When one disconnects at these junctions to inspect them, friction of the corroded spots against each other, or against an uncorroded piece, can temporarily remove the corrosion. This process explains why turning a battery in its slot can make the battery work better temporarily. The corrosion on the battery (or on the connections to it) was invisible, but the corrosion limited current flow until the surfaces rubbed together. Similarly, in other electromagnetic systems, the corrosion could easily be erased temporarily when connectors are unmated prior to inspecting them. For a technique to be effective at identifying corrosion that inhibits current flow, it must detect corrosion prior to unmating the connectors.

X-ray methods are expensive, and the foreign materials they detect in metal junctions may not be corrosion. Further, x-ray methods are not practical for routine testing of field equipment.

The second category includes techniques that attempt to detect the adverse effects caused by corrosion. Two techniques predominate. A Loop Resistance Tester ("LRT") can detect very small resistance in electrical cables and connectors. A Time-Domain Reflectometer ("TDR") can detect discontinuities in electrical conductors, some of which could be caused by severe corrosion.

A LRT cannot identify corrosion as the cause of increased resistance in the current path. Since corrosion problems are often intermittent, resistance measurements generally fail to identify a corrosion problem as it develops.

Thus there exists a need for apparatus and methods for detecting non-intrusively the presence of corrosion in metal to metal junctions.

OBJECTS AND SUMMARY OF THE INVENTION

Therefore, one object of the present invention is to provide apparatus and method to specifically detect the existence of corrosion in metal junctions.

Another object of the present invention is to provide apparatus and method that are non-intrusive to specifically detect the existence of corrosion in metal junctions.

Briefly stated, the present invention provides apparatus and method to detect corrosion in metal junctions. Corroded metal junctions are usually discovered by visual inspection. The present invention detects corrosion in metal junctions when it is not visually apparent. A corroded metal junction acts as a nonlinear device. It generates harmonics and other nonlinear products (such as intermodulation) of any signals applied to the junction. The presence of relatively high level harmonics and/or intermodulation products indicates directly that corrosion has occurred. To detect corrosion in a metal junction, one couples a fundamental frequency signal ($f_o$) into the junction and tests for harmonics of that frequency, especially the third harmonic. Harmonic frequency signals that are relatively large (i.e., above the harmonics generated by the testing system) indicate the presence of corrosion. Measurements to determine if a metal junction is corroded are performed without disturbing the junction.

In an extension of this technique to detect corrosion, couple two (or more) signals into the junction being evaluated and check the output signal for intermodulation products of these signals. Such intermodulation products indicate corrosion on the junction.

According to an embodiment of the invention, apparatus to detect corrosion in a metal-to-metal junction comprises: a signal generator capable of generating at least one electrical signal; a signal injector for injecting the at least one electrical signal into said metal-to-metal junction; a detector effective for detecting the amplitude of the at least one electrical signal, wherein the signal has passed through the metal-to-metal junction, the detector further comprises: an ability to detect the amplitude of at least one selected electrical output signal produced by the non-linear property of a corroded metal-to-metal junction, wherein the presence of a detectable selected electrical output signal amplitude produced by the non-linear property indicates the presence of corrosion; and a signal receiver for receiving the detected amplitude of the at least one electrical output signal from the metal-to-metal junction and for receiving the detected amplitude of at least one selected electrical output signal produced by the non-linear property of a corroded the metal-to-metal junction.

According to a feature of the invention, apparatus to detect corrosion in a metal-to-metal junction comprises a signal generator effective for generating multiple electrical signals each of which has a different frequency; a signal injector for injecting the multiple electrical signals into the metal-to-metal junction; a detector effective for detecting the amplitude of the multiple electrical signals, where the signals have passed through said metal-to-metal junction, the detector further comprises: an ability to detect the amplitude of at least one selected output harmonic of the multiple electrical signals, the selected output harmonic produced by the non-linear property of a corroded metal-to-metal junction, wherein the presence of a detectable output harmonic indicates the presence of corrosion; and a signal receiver for receiving the detected output amplitude of the multiple electrical signals upon being passed-through the metal-to-metal junction and for receiving the detected amplitude of at least one selected output harmonic of the multiple electrical signals produced by the non-linear property of a corroded the metal-to-metal junction.

According to another feature of the invention, a method for detecting corrosion in a metal-to-metal junction comprises the steps of: generating at least one electrical signal; injecting the at least one electrical signal into the metal-to-metal junction; detecting the output amplitude of the at least one electrical signal, wherein the step of detecting further comprises: detecting the amplitude of at least one electrical output signal produced by the non-linear property of a corroded metal-to-metal junction, wherein the presence of a detectable output signal amplitude produced by the non-linear property indicates the presence of corrosion; a first step of receiving the detected amplitude of the at least one electrical output signal having passed through the metal-to-metal junction; and a second step of receiving the detected amplitude of at least one electrical output signal produced by the non-linear property of a corroded metal-to-metal junction.

The present invention offers apparatus and a novel, reliable, non-destructive, non-intrusive method for detecting corrosion in metal junctions. The present invention is based on the nonlinear transmission properties of a corroded metal junction. The present invention detects corrosion in both accessible metal junctions and those that are hidden and therefore inaccessible. The present invention provides a means to detect corrosion when corrosion affects current flow and before significant loss of material occurs.

Most of the embodiments of the present invention do not require disconnecting equipment and electrical cables/connectors for the purpose of testing them. Early detection of corrosion allows replacement of degrading metallic junctions before catastrophic failure results in costly damage to life or property. The present invention also guards against critical electrical system failures that can cause major problems in complex military or commercial systems. Since corrosion is often the cause of electromagnetic interference, the sources of this interference become easier to detect with the present invention. The present invention can be entirely carried out with commercially available, off-the-shelf equipment.

These and many other objects and advantages of the present invention will be readily apparent to one skilled in the pertinent art from the following detailed description of a preferred embodiment of the invention and the related drawings, in which like reference numerals designate the same elements.

DESCRIPTION OF THE PREFERRED EMBODIMENT

When corrosion occurs in a junction between two metallic surfaces, a nonlinear metal-oxide-metal ("MOM") junction is created. If a voltage is applied across the junction, tunneling will occur and the resulting current-voltage relationship will be nonlinear.

A corroded metal junction operates in a nonlinear manner, generating intermodulation products or harmonics of electrical signals that pass through it. For a single input signal, the non-linear products will be the harmonics of the individual signal. For two input signals, the intermodulation products' frequencies are given by the following formula:

$$f_i = |nf_1 \pm mf_2|.$$

In this formula, $f_i$ is the frequency of the intermodulation product, $f_1$ and $f_2$ are the frequencies of the two input signals, and m and n can be any positive integer. This formula can be expanded to cases where there are more than two signals that form intermodulation products.

Figure 1:
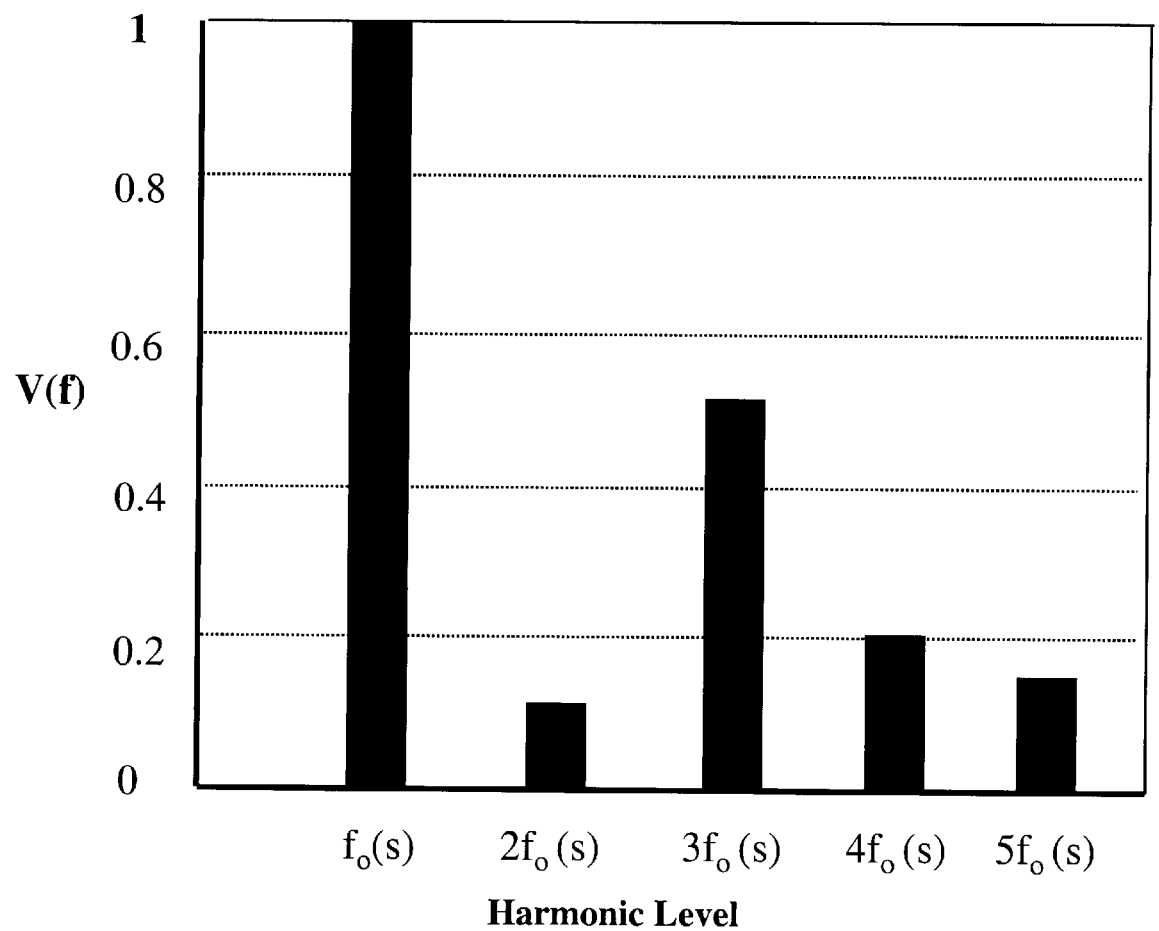
FIG. 1 shows a typical spectrum associated with the non-linearity caused by corrosion at a junction.

Thus, if a single input signal has a fundamental frequency $f_0$, the corroded junction will generate harmonic frequencies $2f_0, 3f_0, 4f_0$, etc. FIG. 1 shows a typical non-linear spectrum associated with corrosion at a junction responding to a single signal. Generally, with corrosion in the current path, the third harmonic frequency ($3f_0$) offers the most pronounced harmonic of the fundamental frequency signal.

Many electromagnetic interference ("EMI") problems result from corroded metal junctions. Some of the major nonlinear effects that occur are: (1) the generation of harmonics of any signal propagating through the junction; (2) the modulation of the signal resulting from time variations in impedance that are due to vibrations or other outside influences that cause intermittent contact; (3) the partial rectification of a strong interfering signal that results in a dc bias level on the signal; and (4) the distortion of the intended signal.

To detect corrosion in a metal junction using the present invention, it is necessary to inject a fundamental frequency signal ($f_0$) into the metal junction under test and monitor the output signal. Harmonic signals relatively high in amplitude (i.e., harmonic signals above the levels generated by the monitor system) indicate the presence of corrosion.

There are a number of ways to inject the fundamental frequency ($f_0$) signals into a metal junction to test for corrosion and to pickup harmonic frequencies (e.g., $3f_0$) caused by corrosion.

Conducted Injection/Pickup. Connect the signal source for injection and the signal receiver for pickup directly to the area near the metal junction under test by a clip, needlepoint probe, etc. Standard EMI measurements are made for conducted injection and pickup. This technique is particularly suited for signal injection and pickup in metal structures and electrical cables/connectors.

Radiated Injection/Pickup. Antennas near the metal junction under test radiate the fundamental test signal ($f_0$) and pick up the third harmonic signal ($3f_0$). Standard EMI measurements are made for radiated injection and pickup. This technique is particularly suited for signal injection and pickup in metal structures.

Current Probe Injection/Pickup. Enclose cables or wires within the current injection and pickup current probe aperture (inductive injection and pickup). This technique is the best for injecting and picking up signals on electrical cable and connector combinations, that is, where a corroded metal junction is located either where a cable or wire joins a connector or between one connector and another. The current probe(s) can be located at any accessible point along the cable or wire under test. This technique allows testing for corrosion at any location within a circuit, provided signal levels are adequate for both the fundamental and third harmonic frequencies and the test instrument's third harmonic is isolated. This technique also uses standard EMI measurements.

This embodiment of the corrosion detection system requires the following conditions to detect a corroded metal junction.

1. The test signal applied to the junction must exceed the threshold voltage for conduction across the junction. This threshold voltage is approximately 0.2 volts.

2. The test setup must have sufficient dynamic range (defined as the difference in level between the third harmonic generated by the test setup and the third harmonic generated by the corroded junction) to indicate clearly that the metal junction under test is corroded. A dynamic range of 50–60 dB is recommended.

3. Operation of the third harmonic receiver is within its normal dynamic range, so that the system shows the third harmonic clearly, and the reference or test signal does not saturate the receiver.

Figure 2:
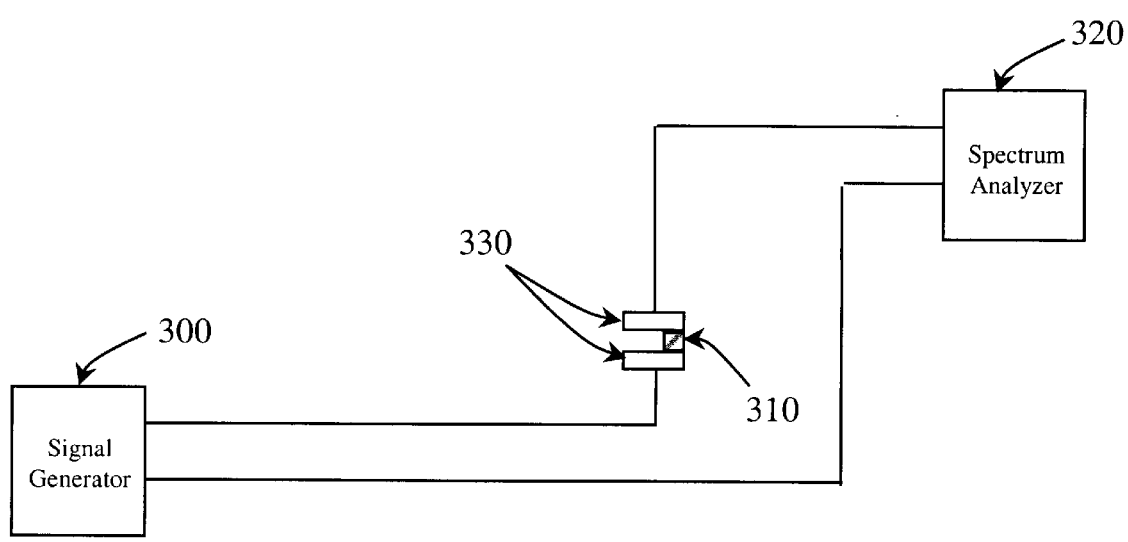
FIG. 2 shows the minimum requirements for the corrosion detection system of the preferred embodiment of the present invention.

Referring to FIG. 2, a signal generator 300 generates a signal at a fundamental frequency $f_0$. This signal passes through a corroded metal-to-metal junction 310. A signal injector/receiver 330 injects the signal and picks up the response. A spectrum analyzer 320 analyzes the signal from the corroded junction. For the invention to be effective, the harmonics of the fundamental frequency signal $f_0$, generated by corroded metal-to-metal junction 310, must be distinguishable from the harmonics generated by signal generator 300 and spectrum analyzer 320. Thus the harmonics generated by corroded metal-to-metal junction 310 must be considerably higher than the noise developed at the same frequency by the test instrumentation. Measurements have demonstrated that the third harmonic ($3f_0$) generated by a corroded metal junction is approximately 36 dB below the level of the fundamental frequency signal ($f_0$) applied to the junction. Thus the amplitude of the third harmonic generated in the test system must be substantially below this value.

Figure 3:
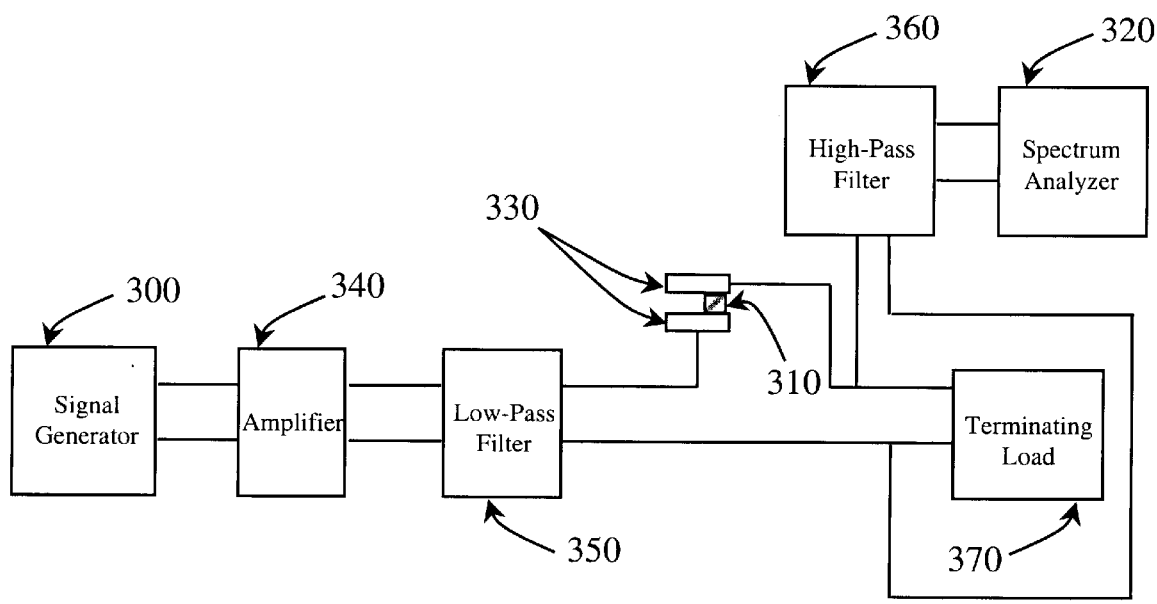
FIG. 3 shows the system of FIG. 2 with additional elements that increase the system's reliability.

Referring to FIG. 3, additions to the system make it reliable for more applications. Low-pass filter 350 modifies the output of signal generator 300. High-pass filter 360 modifies the input to spectrum analyzer 320. These filters significantly reduce the noise generated by the test instruments in the range of the third harmonic of the fundamental signal. An amplifier 340 can also be used to increase the signal level. A terminating load 370 avoids impedance mismatch in the circuit. The dynamic range of this system, even using standard EMI measurement laboratory test equipment, is adequate to detect the harmonics generated by a corroded metal-to-metal junction 310.

Figure 4:
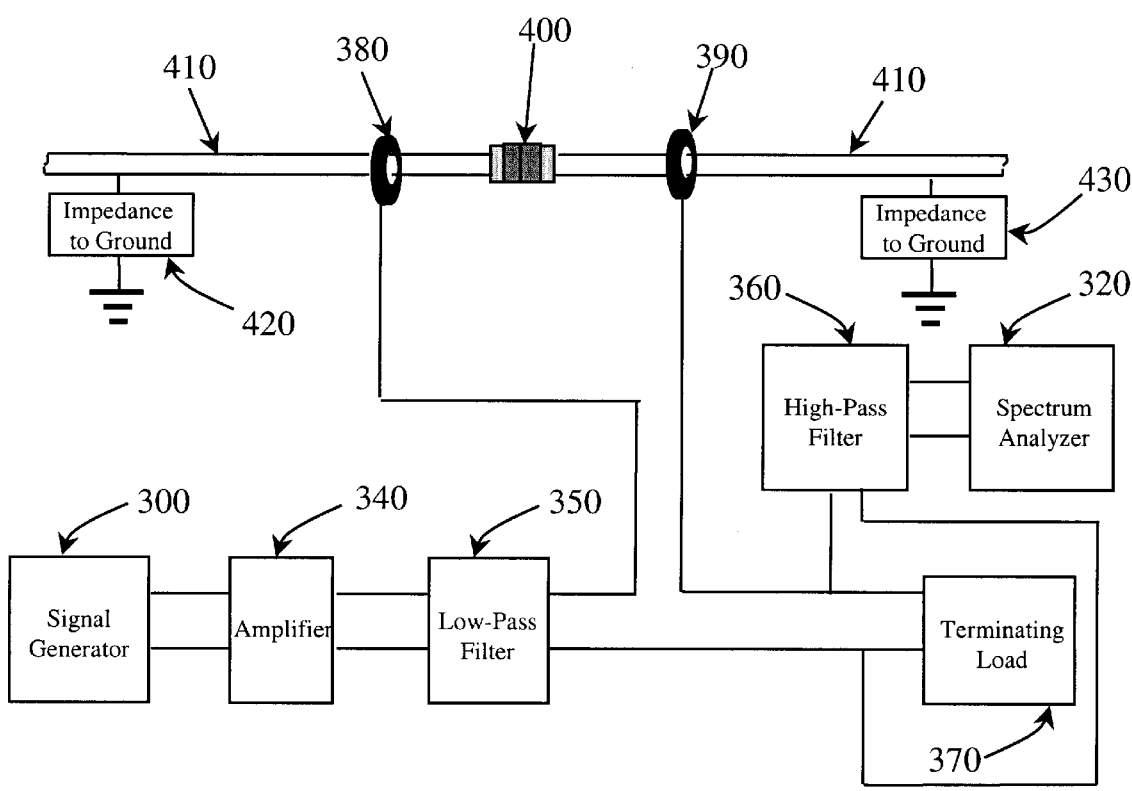
FIG. 4 shows the preferred embodiment of a corrosion detection system applied to detect corrosion at a metal-to-metal junction between electrical connectors.

FIG. 4 shows a preferred embodiment to detect corrosion at the metal-to-metal junction between electrical connectors 400. This system employs the basic configuration shown in FIG. 3. Current probes 380, 390 are clamped around a cable 410 and can inject a signal and read out the response without disconnecting the cable. Current probes 380 and 390 completely encircle cable 410 at two separate points. They can occupy any position along cable 410 and need not be on opposite sides of connectors 400 as shown in FIG. 4. Cable 410 remains connected to the circuit it is part of. This circuit has characteristic impedance to ground represented by 420, 430. If cable 410 is not part of a complete circuit as shown in FIG. 4, the floating ends must be connected to each other through a resistance (e.g., 50 ohms).

The ability to detect corrosion in metal junctions is frequency-dependent. For a specific configuration, the ability to detect corrosion is greater at certain frequencies than at others. For this reason the input signal can be a swept or a stepped frequency to take advantage of this dependence of the corrosion detection system on frequency. It is beneficial to use this frequency dependence to enhance corrosion detection.

Swept- or stepped-frequency inputs maximize the coupling of the test signal into the metal junction under test and maximize the coupling of the third harmonic out of the junction. This enhancement arises from the fact that one range of frequencies typically works best for coupling the test signal into the device under test and another range works best for coupling the signal out of the device. The intersection of these frequency ranges typically produces an optimal frequency at which the third harmonic output is maximized. The optimal test frequency also varies depending on the physical and electrical characteristics of the area near the metal junction under test. For electrical connectors, the configuration of the wires, in the cable that leads to the connector, influences the optimal frequency, as do the properties of those wires, the length and positioning of the cable, and the insulation surrounding the cable (as well as other factors). For larger metal-to-metal junctions, the configuration, physical size, properties, and surroundings of the metal influence the optimal frequency for detecting corrosion. Interference with nearby electronic equipment is another consideration in selecting a range for the swept-frequency input to the device under test.

Referring to FIG. 4, signal generator 300 generates a fundamental test signal ($f_0$) at numerous points throughout a frequency range pre-selected by the user. Spectrum analyzer 320 tracks the response from the metal-to-metal junction, looking for the third harmonic of the input signal ($3f_0$). Signal generator 300 can generate either a swept or a stepped frequency signal. Spectrum analyzer 320 must be able to track and detect the third harmonic of this signal.

The swept- or stepped-frequency system can test for corrosion at a number of RF fundamental frequencies ($f_0$). The best range to detect corrosion in electrical connectors seems to be from 10 MHz to 34 MHz. To include a greater range of electrical and physical structures in and around the corroded metal junction, the input frequency $f_0$ can be reduced to approximately 390 kHz or raised to approximately 100 MHz. An input signal frequency below 390 kHz makes it much harder to inject sufficient levels of signal for testing. Selecting $f_0$ outside this range can cause unwanted effects, such as nonlinear effects and low capacitive reactance to ground that masks positive test results.

The present invention can operate as a computer-controlled stepped-frequency signal source for $f_0$ and a tracking receiver tuned to $3f_0$. When a third harmonic signal ($3f_0$) is detected at a level above the third harmonic frequency signal of the test instrument, a corroded metal junction is the probable cause.

Care must be taken to determine if the third harmonic results from corrosion or from non-linearity in the equipment that the test specimen is connected to. Comparing the output third harmonic to a reference signal from when the equipment was new can help the test operator make this determination. On a cable/connector assembly, another way to verify that the output third harmonic results from corrosion is to disconnect the suspect connectors and reconnect them several times. Repeated disconnection and reconnection can temporarily wipe clean some of the corrosion on the surfaces of metal-to-metal junctions. If the third harmonic output signal shows reduced levels in subsequent tests, then there was significant corrosion on the junctions prior to disconnecting the circuit. However, if there is no change in the output signal after disconnecting and reconnecting the connectors, it should not be interpreted as positively indicating that the connector is corrosion-free. In this case, the disconnecting and reconnecting of the metal junction may not have appreciably cleaned the corroded surfaces.

Still another technique to verify that an elevated third harmonic output results from corrosion on the metal-to-metal junction is to make small movements in the junctions while using the present invention to test for corrosion. Such movements result in the junction making and breaking solid connections through, or around, the corrosion. If the output level of the third harmonic changes significantly during this motion, it is safe to assume that corrosion on the junction is the cause of the elevated $3f_0$ reading.

ALTERNATIVE EMBODIMENTS OF THE PRESENT INVENTION

1. A minimal embodiment is a detector sensitive to the harmonics of the frequency of a signal passing through a junction, but not to the fundamental frequency of the signal. Typically this could be done with a signal generator and a radio receiver with a high-pass filter in series with the corroded junction. An amplifier can also be added to increase the sensitivity of this configuration.

2. Two or more input signals are injected into the junction under test. Corrosion in the signal path will produce intermodulation products of these input signals. Test for output at the frequency of the intermodulation products of the input signals.

3. A single current probe for both input and output of the test signal.

4. Testing with radiated signal input and/or output.

5. Testing with conducted input and/or output.

6. Time domain reflectometry combined with the test technique presented above helps identify the location of the corroded junction.

7. A single frequency input applied to the system instead of a swept- or stepped-frequency input.

8. A harmonic of the input signal other than the third is monitored to indicate corrosion on the metallic junction under test.

9. Several harmonic levels can be combined to form a signature for comparison to the signature of a corrosion-free metallic junction. Significant deviation of this signature from the reference signature indicates corrosion on the metallic junction.

Clearly many modifications of the present invention are possible in light of the above teachings. It should therefore be understood that, within the scope of the inventive concept, the invention may be practiced otherwise than as specifically claimed.

What is claimed is:

1. Apparatus to detect corrosion in a metal-to-metal junction, comprising:
   a signal generator capable of generating at least one electrical signal;
   a signal injector for injecting said at least one electrical signal into said metal-to-metal junction;
   a detector effective for detecting the amplitude of said at least one electrical signal, said signal having passed through said metal-to-metal junction, said detector further comprising:
     an ability to detect the amplitude of at least one selected electrical output signal produced by the non-linear property of a corroded said metal-to-metal junction, wherein the presence of a detectable said selected electrical output signal amplitude produced by said non-linear property indicates the presence of corrosion; and
   a signal receiver for receiving said detected amplitude of said at least one electrical signal from said metal-to-metal junction and
     for receiving said detected amplitude of at least one selected electrical output signal produced by said non-linear property of a corroded said metal-to-metal junction.

2. Apparatus as in claim 1, wherein said at least one selected detectable electrical signal amplitude produced by said non-linear property of a corroded said metal-to-metal junction is produced by at least two said electrical input signals.

3. Apparatus as in claim 1, wherein said signal generator is effective to suppress generation of said at least one selected electrical output signal amplitude produced by said non-linear property of a corroded said metal-to-metal junction.

4. Apparatus as in claim 1, wherein said detector includes a filter effective to substantially attenuate any electrical signal except said at least one selected electrical output signal produced by said non-linear property of a corroded said metal-to-metal junction.

5. Apparatus as in claim 1, wherein said detector is further effective to substantially attenuate any electrical signal, generated by any other portion of test circuitry, except said at least one selected electrical output signal produced by said non-linear property of a corroded said metal-to-metal junction.

6. Apparatus as in claim 1, wherein said metal-to-metal junction further comprises a pair of electrical connectors.

7. Apparatus as in claim 1, wherein said at least one electrical input signal is a single signal and said at least one selected detectable electrical signal amplitude produced by said non-linear property of a corroded said metal-to-metal junction is at least one harmonic thereof.

8. Apparatus to detect corrosion in a metal-to-metal junction, which comprises:
   a signal generator effective for generating multiple electrical signals each of which has a different frequency;
   a signal injector for injecting said multiple electrical signals into said metal-to-metal junction;
   a detector effective for detecting the amplitude of said multiple electrical signals, said signals having passed through said metal-to-metal junction, said detector further comprising:
     an ability to detect the amplitude of at least one selected output harmonic of said multiple electrical signals, said selected output harmonic produced by the non-linear property of a corroded said metal-to-metal junction, wherein the presence of a detectable output harmonic indicates the presence of corrosion; and
   a signal receiver for receiving said detected output amplitude of said multiple electrical signals upon being passed-through said metal-to-metal junction and
     for receiving said detected amplitude of at least one selected output harmonic of said multiple electrical signals produced by the non-linear property of a corroded said metal-to-metal junction.

9. Apparatus as in claim 8, wherein said multiple electrical signals are input sequentially and swept in frequency.

10. Apparatus as in claim 9, wherein said signal generator is effective to suppress generation of said at least one of said selected harmonics of said multiple electrical signals.

11. Apparatus as in claim 9, wherein said detector includes a filter effective to substantially attenuate any signal except said at least one of said selected harmonics of said multiple electrical signals.

12. Apparatus as in claim 9, wherein said detector is further effective to substantially attenuate any electrical signal, generated by any other portion of test circuitry, except said at least one of said selected harmonics of said multiple electrical signals.

13. Apparatus as in claim 9, wherein said metal-to-metal junction further comprises a pair of electrical connectors.

14. Apparatus as in claim 9, wherein at least one of said multiple electrical signals has at least one harmonic whose detection by said detector indicates the presence of corrosion in said metal-to-metal junction.

15. Apparatus as in claim 9, wherein at least two of said multiple electrical signals, said at least two signals being simultaneously input, produce an intermodulation product whose amplitude detection by said detector indicates the presence of corrosion in said metal-to-metal junction.

16. Apparatus as in claim 9, wherein said multiple electrical signals are input sequentially and stepped in frequency.

17. A method for detecting corrosion in a metal-to-metal junction, which comprises the steps of:

generating at least one electrical signal;

injecting said at least one electrical signal into said metal-to-metal junction;

detecting the output amplitude of said at least one electrical signal, said step of detecting further comprising:
  detecting the amplitude of at least one electrical output signal produced by the non-linear property of a corroded said metal-to-metal junction, wherein the presence of a detectable output signal amplitude produced by said non-linear property indicates the presence of corrosion;

a first step of receiving said detected amplitude of said at least one electrical output signal having passed through said metal-to-metal junction; and a second step of receiving said detected amplitude of said at least one electrical output signal produced by the non-linear property of a corroded said metal-to-metal junction.

18. The method of claim 17, wherein said step of generating at least one electrical signal further comprises a step of generating multiple signals swept in frequency.

19. The method of claim 17, wherein said step of generating at least one electrical signal further comprises a step of generating multiple signals stepped in frequency.

* * * * *